United States Patent
Proksa

(10) Patent No.: US 8,265,223 B2
(45) Date of Patent: Sep. 11, 2012

(54) DATA ACQUISITION

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/003,320

(22) PCT Filed: Jul. 14, 2009

(86) PCT No.: PCT/IB2009/053047
§ 371 (c)(1),
(2), (4) Date: Jan. 10, 2011

(87) PCT Pub. No.: WO2010/015951
PCT Pub. Date: Feb. 11, 2010

(65) Prior Publication Data
US 2011/0135052 A1   Jun. 9, 2011

Related U.S. Application Data

(60) Provisional application No. 61/085,890, filed on Aug. 4, 2008.

(51) Int. Cl.
*A61B 6/00* (2006.01)
(52) U.S. Cl. .................. 378/9; 378/4; 382/131
(58) Field of Classification Search .................. 378/4, 9
See application file for complete search history.

(56) References Cited

U.S. PATENT DOCUMENTS

| | | | | |
|---|---|---|---|---|
| 4,052,620 | A * | 10/1977 | Brunnett | 378/97 |
| 4,097,793 | A * | 6/1978 | Shapiro et al. | 324/403 |
| 4,277,683 | A * | 7/1981 | Schmitmann | 378/98 |
| 4,825,077 | A * | 4/1989 | Tawil et al. | 250/369 |
| 5,173,852 | A * | 12/1992 | Lonn | 378/9 |
| 5,249,123 | A * | 9/1993 | Hsieh | 378/19 |
| 5,331,682 | A * | 7/1994 | Hsieh | 378/19 |
| 5,490,218 | A * | 2/1996 | Krug et al. | 382/100 |
| 6,671,345 | B2 | 12/2003 | Vrettos et al. | |
| 2004/0264626 | A1 * | 12/2004 | Besson | 378/4 |
| 2006/0250291 | A1 | 11/2006 | Lyden et al. | |
| 2007/0005278 | A1 * | 1/2007 | Brunnett | 702/78 |

FOREIGN PATENT DOCUMENTS

| WO | 2006072847 A1 | 7/2006 |
|---|---|---|
| WO | 2008053403 A2 | 5/2008 |

* cited by examiner

*Primary Examiner* — Alexander H Taningco

(57) ABSTRACT

An imaging system includes at least one radiation generating component (210) that alternately emits different radiation that traverse an examination region and a common detector (214) that detects radiation that traverses the examination region and generates a signal indicative thereof. Pulse generating circuitry (304) generates a pulse train, including a plurality of pulses, with a frequency indicative of the signal for the at least one radiation generating component (210) for a sampling interval. Processing electronics (220) determine an approximation of the signal for one of the at least one radiation generating components (210) for the sampling interval based on a number of pulses in the pulse train for the sampling interval and charge of the pulses in the pulse train.

25 Claims, 5 Drawing Sheets

DATA ACQUISITION

CROSS REFERENCE TO RELATED APPLICATIONS

This application claims the benefit of U.S. provisional application Ser. No. 61/085,890 filed Aug. 4, 2008, which is incorporated herein by reference.

The following generally relates to data acquisition, and finds particular application to computed tomography (CT). However, it also amenable to other medical imaging applications and to non-medical imaging applications.

A stereo tube computed tomography (CT) scanner includes two x-ray tubes mounted on a rotatable gantry that rotates around an examination region about a z-axis. The two x-ray tubes are arranged with respect to each other such that they are disposed on the rotating gantry at about a same angular position and offset from each other along the z-axis. A detector array subtends an angular arc opposite the examination region from the x-ray tubes and detects radiation that traverses the examination region for a plurality of sampling or integration intervals. For each sampling interval and for each tube, the detector array generates a signal indicative of the examination region. A reconstructor reconstructs the signals to generate volumetric image data thereof, which can be used to generate an image of a subject or object disposed in the examination region.

The detector array has included a scintillator, a photodiode and processing electronics. The scintillator absorbs radiation and produces light indicative of the absorbed radiation, and the photodiode receives the light and produces a signal such as an electrical current or voltage indicative of the light and, hence, the detected radiation. The processing electronics have also included a current-to-frequency converter that samples the current and produces a corresponding train of pulses with a frequency indicative of the amplitude of the current. The processing electronics have determined the output current of the photodiode for a sampling interval by multiplying the number of pulses in a sampling interval by the charge of the pulses. Unfortunately, if the last pulse in a sampling interval does not align with the boundary between successive sampling intervals, the charge for that sampling interval will erroneously contribute to the photodiode current measurement for the next sampling interval. This residual charge that carries over into the next sampling interval is referred to as Delta Data.

For clarity, the foregoing is illustrated by way of the timing diagrams shown in FIG. 1. The timing diagram begins within a first sampling interval. The gate signal GS1, which controls the x-ray flux FL1 of a first x-ray tube, is "on," or in a state in which the first radiation source emits radiation. The gate signal GS2, which controls the x-ray flux FL2 of a second x-ray tube, is "off," or in a state in which the second x-ray tube does not emits radiation, and the effective flux FL2 is zero. Up to t1, the photodiode detects radiation emitted by the first x-ray tube and produces output charge I. The current I is integrated, and a current-to-frequency converter generates pulses PS at a frequency indicative of the amplitude of the charge I. At t1, the gate signal GS1 is turned "off," or transitions to a state where the first x-ray tube no longer emits radiation.

From t1 to t2, an effective x-ray flux FL1 of the first x-ray tube decreases, decreasing the output current I and, hence, the frequency at which the pulses PS are generated. At t2, the effective flux FL1 is zero, and scintillator afterglow exponentially decays, decreasing the output current I and, hence, the frequency at which the pulses PS are generated. At t3, the first sampling interval ends and the next sampling interval begins as gate signal GS2, which controls the x-ray flux of a second x-ray tube, is turned "on." Shortly thereafter, an effective x-ray flux FL2 of the second x-ray tube increases, and the current output I for the second x-ray tube increases. Again, the current-to-frequency generates pulses PS at a frequency indicative of the output current I of the photodiode, and the above repeats.

As noted above, the processing electronics determine the output current of the photodiode for a sampling interval by multiplying the number of pulses in a sampling interval by the charge of a pulse. However, as shown in FIG. 1 the last pulse in the first sampling interval, pulse 102, occurs prior to the end of the first sampling interval t3, and the next pulse, pulse 104, is the first pulse in the next sampling interval. As a consequence, the charge corresponding to the interval from the pulse 102 to the pulse 104 contributes to the charge measurement for both the first sampling interval and the second sampling interval, even though this charge corresponds only to the first sampling interval. Thus, when the generated pulses do not align with the boundary (t3) between successive sampling intervals, as shown in FIG. 1, then the Delta Data problem is generated, and charge from one sampling interval contributes to the charge of a succeeding sampling interval, corrupting the charge measurement of the succeeding sampling interval.

Aspects of the present application address the above-referenced matters and others.

According to one aspect, an imaging system includes at least one radiation generating component that alternately emits different radiation that traverse an examination region and a common detector that detects radiation that traverses the examination region and generates a signal indicative thereof. Pulse generating circuitry generates a pulse train, including a plurality of pulses, with a frequency indicative of the signal for the at least one radiation generating component for a sampling interval. Processing electronics determine an approximation of the signal for one of the at least one radiation generating components for the sampling interval based on a number of pulses in the pulse train for the sampling interval and charge of the pulses in the pulse train. The processing electronics calculates a first contribution to the approximation for a first range of pulses from a first pulse in the sampling interval to a last pulse in the sampling interval, and estimates a second contribution to the approximation for a second range of pulses from the last pulse in the sampling interval to an end of the sampling interval. The second contribution is estimated based on charge for the first contribution, wherein charge for the second contribution is unavailable.

According to another aspect, a method includes detecting first radiation being emitted only during a first sub-set of a first sampling interval, generating a signal indicative of the detected radiation and of a decaying afterglow signal produced during a second subsequent sub-set of the first sampling interval in which the first radiation is not being emitted, integrating the signal to generate an integrated signal, clearing the integrated signal during the second sub-set of the first sampling interval, generating pulses for the first sampling interval with a frequency indicative of the integrated signal, and determining an approximation of the signal based on the generated pulses, including calculating a first contribution for a first time period of the first sampling interval up to the clearing of the integrated signal and estimating a second contribution for a second time period of the first sampling period after the clearing of the integrated signal.

According to another aspect, a stereo tube imaging system includes first and second radiation sources arrange at about a same angle and offset along a z-axis direction, wherein the first radiation source emits first radiation during a first integration interval and the second radiation source emits second radiation during a second integration interval. A detector array detects the emitted radiation and generates a signal indicative thereof. Integrating circuitry integrates the signal. A resetter resets the integrating circuitry prior to an end of each integration interval. Pulse generating circuitry generates a pulse train, including a plurality of pulses, with a frequency indicative of the signal for each integration interval. A partial charge determiner determines charge for a first portion of the first integration interval up to a last pulse before the reset based on a number of pulses in the first integration interval up to the last pulse, and a missing charge determiner determines charge for a second portion of the first integration interval that begins with the last pulse.

According to another aspect, a method for approximating a signal indicative of detected radiation over a sampling interval includes generating pulses with a frequency indicative of an integration of the signal, calculating a first contribution from a first pulse to a last pulse in the sampling interval, calculating a second contribution after the last pulse based on a decay constant determined from the sampling interval, calculating a total contribution by adding the first and second contributions.

The invention may take form in various components and arrangements of components, and in various steps and arrangements of steps. The drawings are only for purposes of illustrating the preferred embodiments and are not to be construed as limiting the invention.

Figure 1:
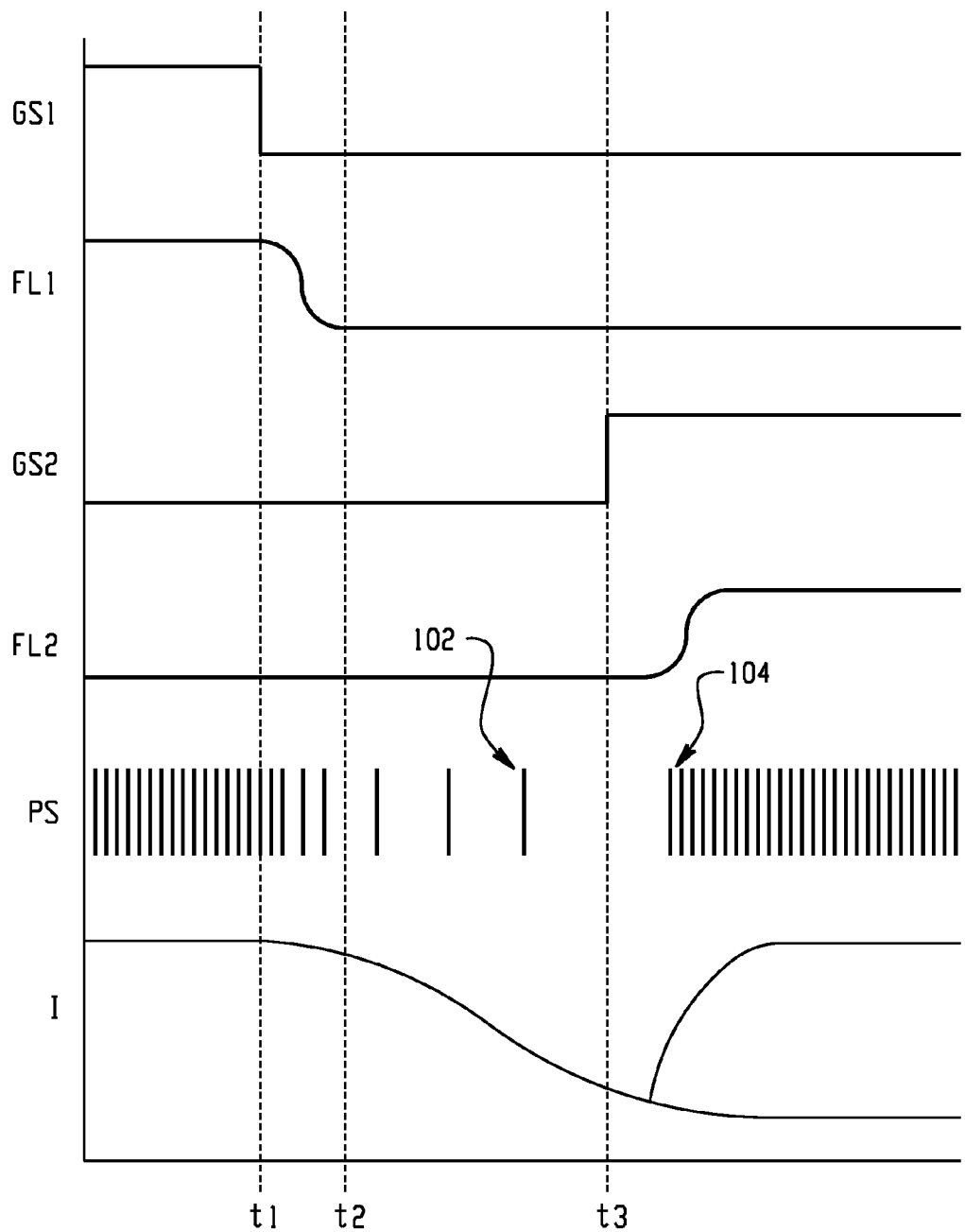
FIG. 1 illustrates prior art timing diagrams showing Delta Data in connection with a stereo tube CT scanner.
Figure 2:
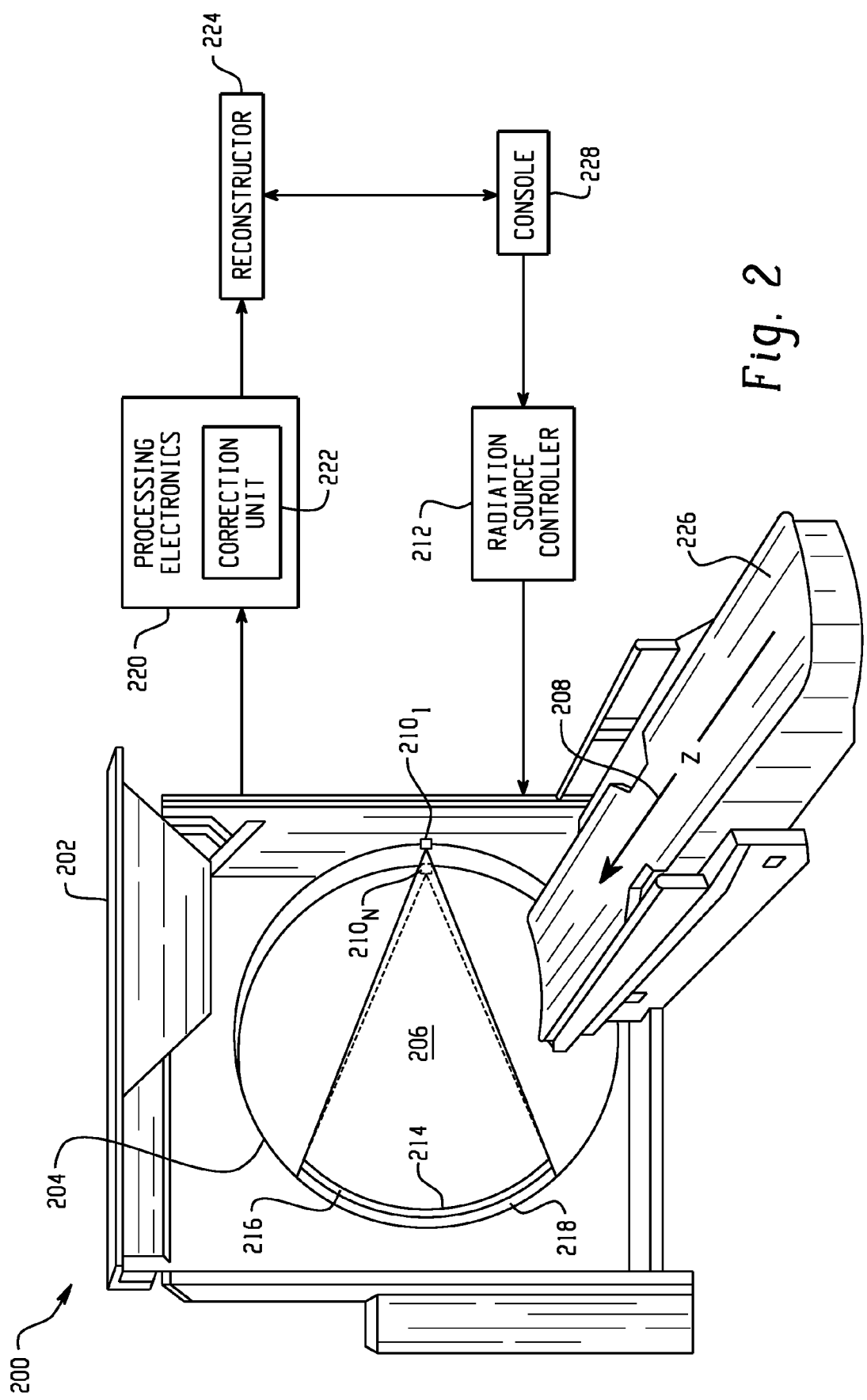
FIG. 2 illustrates an example imaging system.

FIG. 2 illustrates a computed tomography (CT) scanner 200 that includes a stationary gantry 202 and a rotating gantry 204, which is rotatably supported by the stationary gantry 202. The rotating gantry 204 rotates around an examination region 206 about a longitudinal or z-axis 208.

The scanner 200 includes N radiation sources $210_1$, $210_N$ (collectively referred to herein as radiation sources 210), wherein N is an integer greater than one. At least two of the radiation sources 210 are arranged with respect to each other in a stereo configuration, being disposed on the rotating gantry 204 at about a same angular position around the examination region 206 and offset along a z-axis direction 208. The radiation sources 210 emit radiation, which traverses the examination region 206. A collimator collimates the emitted radiation to produce a generally fan, wedge, or cone shaped radiation beam that traverses the examination region 206. It is to be appreciated that the radiation sources 210 may originate from different x-ray tubes or the same x-ray tube.

A radiation source controller 212 controls the radiation sources 210. Such control includes, but is not limited to, selectively activating (turning on to emit radiation) and deactivating (turning off) the radiation sources 210. The controller 212 alternately activates the radiation sources 210 so that only one of the sources 210 emits radiation at any given time. This can be done through grid switching, a filter, or otherwise. In one instance, such control may include activating the radiation sources 210 at less than a 100% duty cycle. When configured as such, a radiation "off" period, in which radiation is not emitted, exists between radiation "on" phases. It is to be appreciated that the radiation "off" period may facilitate mitigating afterglow artifact in a subsequent sampling or integration interval as the afterglow signal has time to decay to some extent during this radiation "off" period before the next sampling interval.

A radiation sensitive detector array 214 subtends an angular arc opposite the examination region 206 from the radiation sources 210 and includes a scintillator array 216 and one or more rows of photosensors 218, such as photodiodes or other photosensors. In other embodiments, the scanner 200 includes a direct conversion material. For explanatory purposes, processing electronics 220 are shown separate from the detector array 214. However, it is to be understood that the processing electronics can be part of the detector array 214. The processing electronics 220 produce a signal that is indicative of the output of the photosensor 218. As described in greater detail below, this may include employing a correction unit 222, which at least corrects for any Delta Data, if needed.

A reconstructor 224 reconstructs the signal and generates volumetric image data indicative thereof, which can be used to generate one or more images. A patient support 226, such as a couch, supports an object or subject such as a human patient in the examination region 206. A general purpose computing system serves as an operator console 228. Software resident on the console 228 allows the operator to control the operation of the system 200.

Figure 3:
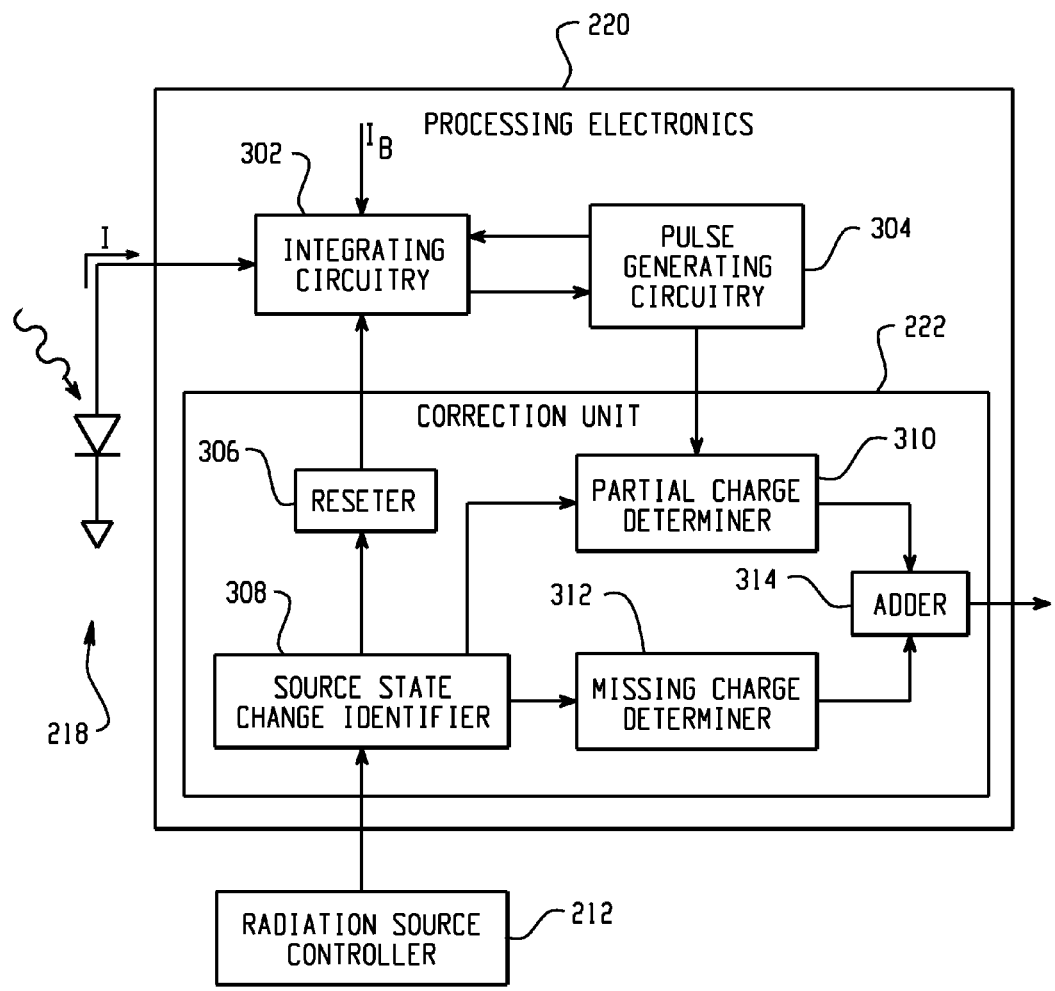
FIG. 3 illustrates example processing electronics.

FIG. 3 illustrates example non-limiting processing electronics 220. Integrating circuitry 302 integrates charge produced by the photosensor 218, for each of the radiation sources 210, along with a bias current $I_B$. Pulse generating circuitry 304 generates a train of multiple pulses, based on the output of the integrating circuitry 302, with a frequency indicative of the charge produced by the photosensor 218. The pulse generating circuitry 304 also generates compensation pluses that are fed back to the integrating circuitry 302. Such pulses generally are generated such that the integral becomes close to zero. Examples of such electronics are described in connection with, but are not limited to, U.S. Pat. No. 4,052,620 to Brunnett, filed Nov. 28, 1975, and entitled "Method and Apparatus for Improved Radiation Detection in Radiation Scanning Systems," and U.S. Pat. No. 6,671, 345 B2 to Vrettos et al., filed Nov. 7, 2001, and entitled "Data Acquisition for Computed Tomography."

The correction unit 222 includes a reseter 306 that generates a signal that resets the integrating circuitry 302. In one instance, the signal is generated based on the deactivation of one of the radiation sources 210 and the delay therefrom to the activation of another one of the radiation sources 210, with the reset generally occurring before activation of the other radiation source 210, or before the start of the next sampling interval. As a result, there is no residual charge or Delta Data that would otherwise erroneously contribute to the next sampling interval. The correction unit 222 also includes a source state change identifier 308 that identifies a state change (deactivation and activation) of the radiation sources 210, for example, from the controller 212 or otherwise.

A partial charge determiner 310 determines the charge output of photosensor 218 based on the pulses for a first sub-portion of the first sampling interval, for example, from the beginning of the first sampling interval to the pulse before the reset by the reseter 306. The pulses are provided by the pulse generating circuitry 304. A missing charge determiner 312 determines or estimates the missing or remaining charge for the sampling interval, which, in this case, begins with the pulse before the reset. The missing charge can be determined based on the decay of the afterglow, which is known, for example, through measurement or otherwise, estimated, for example, as an exponential decay, and/or otherwise determined. In one instance, based on the afterglow decay, the missing charge is determined via extrapolation, for example, from the data corresponding to the first pulse after the flux decreases to zero to the last pulse before the reset.

An adder 314 adds the charge determined by the partial charge determiner 310 and the missing charge determiner 312 to determine the charge produced by the photosensor 218 for each integration interval.

Figure 4:
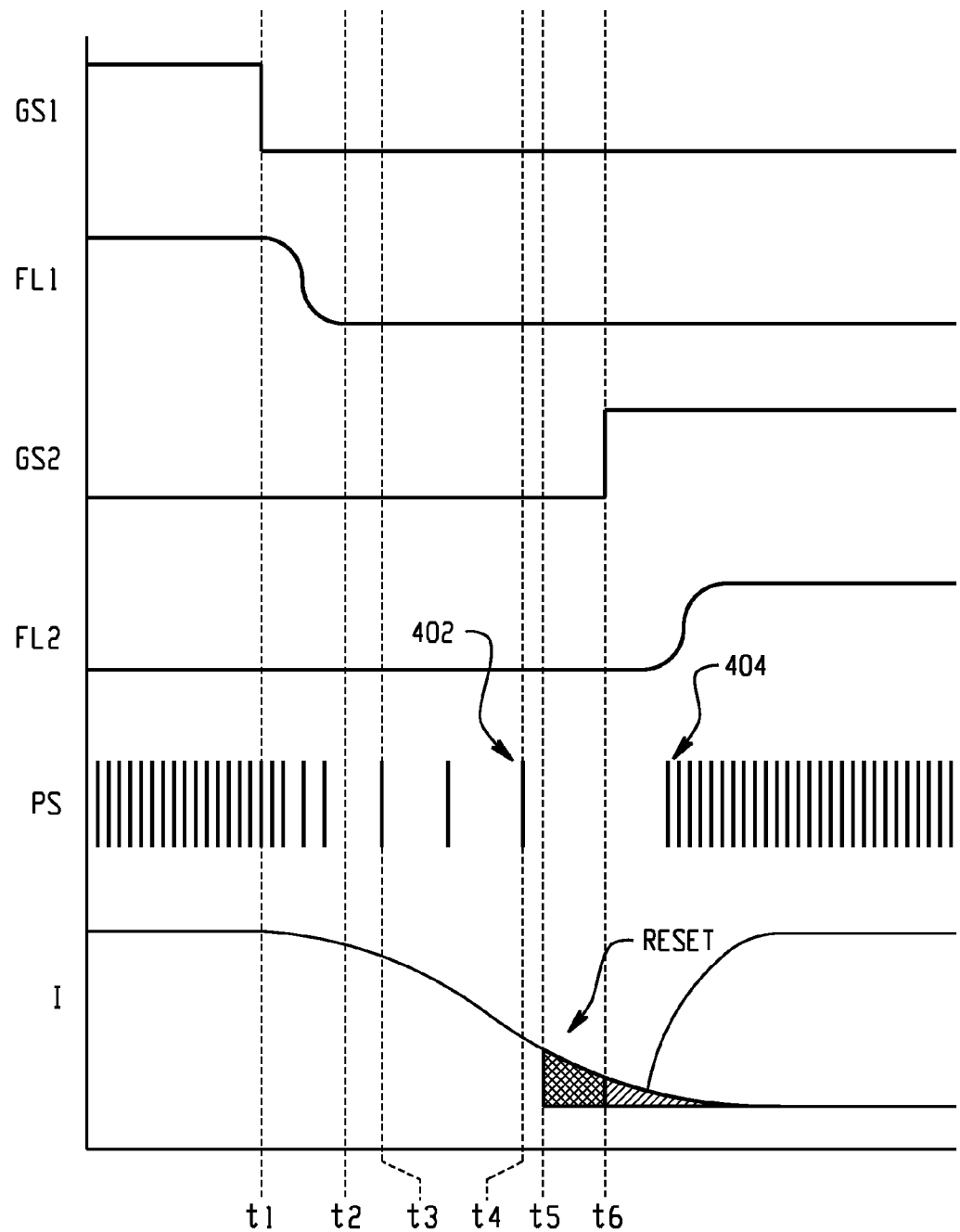
FIG. 4 illustrates timing diagrams.

Operation is described in connection with an example non-limiting timing diagram illustrated in FIG. 4. The timing diagram begins within a first sampling interval. As shown, a gate signal GS1 that controls the x-ray flux FL1 of a first radiation source 210 is "on," or in a state in which the first radiation source 210 emits radiation. A gate signal GS2 that controls the x-ray flux FL2 of a second radiation source 210 is "off," or in a state in which the second first radiation source 210 does not emits radiation, and the flux FL2 is zero. Up to t1, the output charge I of the photosensor 218 for the first radiation source 210 is integrated, and the pulse generating circuitry 304 generates pulses PS at a frequency indicative of the charge I. At t1, the gate signal GS1 is turned "off," or transitions to a state where the first radiation source is "off" or deactivated to turn off radiation emission from the first radiation source 210.

From t1 to t2, an effective x-ray flux FL1 of the first radiation source decreases, decreasing the output current I of the photosensor 218, and, as a result, the pulses PS are generated at a lower frequency. At t2, the scintillator afterglow exponentially decays, decreasing the output current I, and the pulses PS continue to be generated at a lower and lower frequency. At t3, the first pulse is generated after the flux FL1 becomes zero. At t4, a last pulse 402 in the first sampling interval is generated. Shortly thereafter, at t5, the reseter 306 resets the integrating circuitry 302, which clears the integrating circuitry 302 until the next sampling interval, which begins at t6. Although shown beginning at t5, the reset can begin any time between t4 and t6 where the integrating circuitry 302 can be cleared and ready to integrate during the next sampling interval.

At t6, the gate signal GS2 turns "on," or transitions to a state in which the second radiation source 210 emits radiation. Shortly thereafter, an effective x-ray flux FL2 of the second radiation source 210 increases, the output current I of the photosensor 218 for the second radiation source 210 increases, and the pulse generating circuitry 304 generates pulses PS at a frequency indicative of the output of the photosensor 218 for the second radiation source 210.

By resetting the integrating circuitry 302 at t5, Delta Data, or charge corresponding to the interval between pulses 402 and 404, which would otherwise exist and erroneously contribute to the next sampling interval, is mitigated. However, the reset also results in missing charge for the first sampling interval, namely, the charge beginning at t4, which is where the last pulse before the reset is generated. As noted above, the missing charge determiner 312 determines or estimates the missing charge. Since the afterglow decay is known and the afterglow interval t3-t4 is measured, the missing charge can be determined based on Equation 1:

$$Q_{MISSING} = \frac{nQ_p - (t_4 - t_3)i_B}{e^{(t_4-t_3)c} - 1} \quad \text{Equation 1}$$

wherein n is the number of pulses during interval $t_3$-$t_4$, $Q_P$ is the charge of a pulse, and c is the exponential decay constant for the afterglow. As noted above, the adder 314 adds this estimated missing charge and the charge up to t4 to generate a measured value for the output charge of the photodiode 218 for each sampling interval for each radiation source 210.

Optionally, the afterglow charge (beginning at t6) for the next sampling interval is estimated and used to correct for the afterglow. This can be done by the missing charge determiner 312 or other component. Similar to the missing charge, the afterglow charge can be determined based on the exponential decay during the interval t3-t4. In another instance, the charge for the interval t4-t5 is measured and additionally or alternatively used to determine the afterglow charge for the next sampling interval.

It is to be appreciated that in another embodiment, the correction unit 222 can identify when the correction is to be performed. For example, the correction unit 222 can identify when a generated pulse aligns with or substantially aligns with the boundary (t3) between successive sampling intervals. In this instance, the correction can be omitted. Alternatively, the correction can still be performed since it may mitigate afterglow effects in the next sampling interval. However, when a generated pulse does not align with the boundary (t3) between successive sampling intervals, then the correction described herein can be performed. It is also to be appreciated that the results of the correction can be validated and/or used to set and/or adjusts the parameters, such as the reset point, the decay constant, etc. of the correction.

Figure 5:
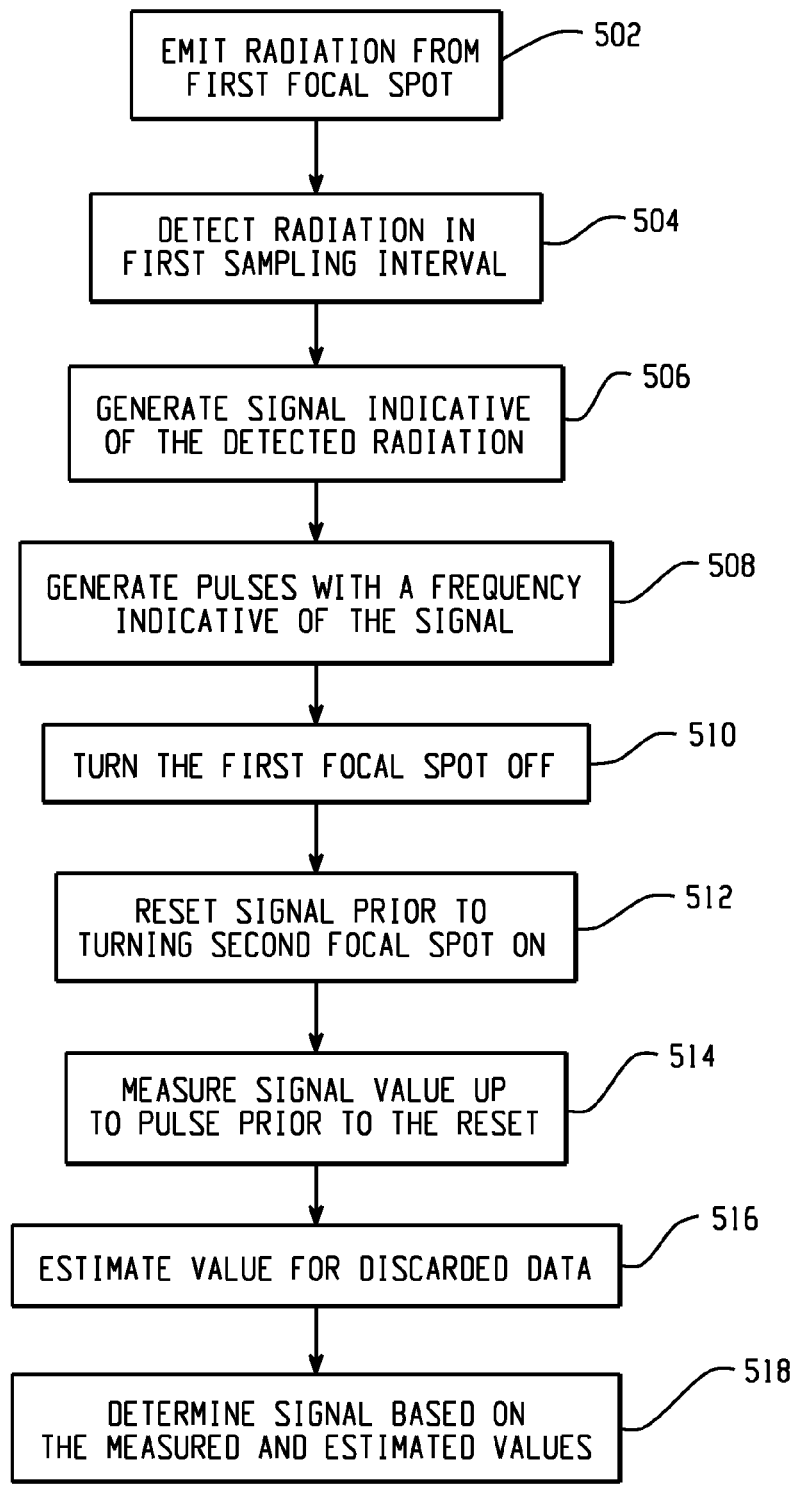
FIG. 5 illustrates an example method.

FIG. 5 illustrates a method. At 502, radiation is emitted from a first focal spot. At 504, the radiation is detected for a first integration sampling interval. At 506, an electrical signal indicative of the detected radiation is generated. At 508, the signal is integrated and a train of pulses with a frequency indicative of the signal is generated based on the integrated signal. At 510, the radiation is turned off. At 512, the signal is reset or cleared prior to the next integration interval. At 514, the value of the electrical signal up to the reset is measured for example as described herein. At 516, data missing for the first integration interval due to the clearing of the signal is estimated for example as described herein. At 518, the value of the electrical signal is determined based on the measured and the estimated values. Optionally, an afterglow signal is estimated as described herein and used to compensate for afterglow in the next integration interval.

Although the above is described in connection with switching between tubes in a stereo tube system, it is to be appreciated that the above can be used with any system in which the detectors detect radiation other than a single emission from the same focal spot. For example, other systems may include employing KVp switching to switch between to different emission spectrums. Such switching can be done through changing the tube voltage or selectively inserting a filter between the beam and the detectors to effectively change the KVp. In another example, the system may include a dual foci tube in which the foci are switched or alternately activated during scanning Other systems are also contemplated.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

I claim
1. An imaging system, comprising:
at least one radiation generating source that is selectively turned on and off so as to alternately emit radiation that traverse an examination region;
a common detector that detects radiation that traverses the examination region and generates a signal indicative thereof;
pulse generating circuitry that generates a pulse train, including a plurality of pulses, with a frequency indicative of the signal; and
processing electronics that determine an approximation of the signal for the at least one radiation generating source for a sampling interval based on a number of pulses in the pulse train for the sampling interval and charge of the pulses in the pulse train, wherein the processing electronics calculate a first contribution to the approximation for a first range of pulses from a first pulse in the sampling interval to a last pulse in the sampling interval, and estimates a second contribution to the approximation for a second range of pulses from the last pulse in the sampling interval to an end of the sampling interval, wherein the second contribution is estimated based on charge from the first contribution.

2. The imaging system of claim 1, further including:
integrating circuitry that integrates the signal generated by the common detector, wherein the pulse generating circuitry generates the pulse train based on the integrated signal; and
a reseter that resets the integrating circuitry after the last pulse in the sampling interval, thereby discarding the charge for the second contribution to the approximation.

3. The imaging system of claim 2, wherein discarding the charge for the first sampling interval mitigates carrying over the charge when determining a second approximation of a signal for a succeeding sampling interval for a different radiation.

4. The imaging system of claim 2, wherein the reseter resets the integrating circuitry before a next sampling interval so that the integrating circuitry is ready to integrate a next signal generated for the next sampling interval.

5. The imaging system of claim 1, further including:
a missing data determiner that estimates the second contribution based on a first decay constant of the common detector and charge indicative of a first decay interval of the common detector during which radiation emitted by the at least one radiation generating components does not traverse the examination region.

6. The imaging system of claim 5, further including:
that selectively alternately activates the at least one radiation generating source, wherein the controller delays activation of a second radiation generating source, after deactivating a first source, for a delay time period, and the decay constant corresponds to charge decay during at least a sub-portion of the delay time period.

7. The imaging system of claim 1, further including:
an adder that adds the first and second contributions together to generate the approximated signal.

8. The imaging system of claim 1, further including:
a component that estimates an afterglow contribution to a subsequent sampling interval based on a second decay constant of the common detector and charge indicative of a second decay interval of the common detector during which radiation generated by the at least one radiation generating component does not traverse the examination region.

9. The imaging system of claim 8, wherein the estimated afterglow contribution is subtracted from the charge in the subsequent sampling interval.

10. The system of claim 1, wherein the at least one radiation generating source includes two radiation generating sources in a stereo tube configuration, wherein each radiation generating source alternately emits radiation.

11. The system of claim 1, wherein the at least one radiation generating source includes a single radiation generating source that alternately emits radiation having different emission spectrums.

12. The system of claim 11, wherein the different emission spectrums correspond to different source emission voltages.

13. The system of claim 11, wherein the different emission spectrums correspond to different filters disposed in a path of the radiation.

14. The system of claim 1, wherein charge for the second contribution is unavailable.

15. A method, comprising:
detecting first radiation being emitted during a first sub-set of a first sampling interval;
generating a signal indicative of the detected radiation and of a decaying afterglow signal produced during a second subsequent sub-set of the first sampling interval in which the first radiation is not being emitted;
clearing the integrated signal during a third subsequent sub-set of the first sampling interval;
integrating the signal over the first, second and third sub-sets to generate an integrated signal;
generating pulses for the first sampling interval with a frequency indicative of the integrated signal; and
determining, with processing electronics of an imaging system, an approximation of the signal based on the generated pulses, including calculating a first contribution for a first time period of the first sampling interval up to the clearing of the integrated signal and estimating a second contribution for a second time period of the first sampling period beginning with the clearing of the integrated signal.

16. The method of claim 15, further including clearing the integrated signal after the last pulse is generated for the first sampling interval.

17. The method of claim 15, further including calculating the first contribution based on a number of pulses for the first sub-set of the first sampling interval, beginning with a first pulse generated for the first sampling interval and ending with a last pulse generated before the clearing, and a charge of a pulse.

18. The method of claim 15, further including estimating the second contribution based on a number of pulses for a second time period from a last pulse prior to the decaying afterglow signal to a last pulse before the clearing of the integrated signal.

19. The method of claim 15, further including estimating an afterglow correction signal for a subsequent sampling interval based on the decaying afterglow signal.

20. A stereo tube imaging system, comprising:
first and second radiation sources arrange at about a same angle and offset along a z-axis direction, wherein the first radiation source emits first radiation during a first integration interval and the second radiation source emits second radiation during a second integration interval;
a detector array that detects the emitted radiation and generates a signal indicative thereof;
integrating circuitry that integrates the signal;
a reseter that resets the integrating circuitry prior to an end of each integration interval;
pulse generating circuitry that generates a pulse train, including a plurality of pulses, with a frequency indicative of the signal for each integration interval; and
a partial charge determiner that determines charge for a first portion of the first integration interval up to a last pulse before the reset based on a number of pulses in the first integration interval up to the last pulse; and
a missing charge determiner that determines charge for a second portion of the first integration interval that begins with the last pulse of the integration interval and ends at an end of the integration interval.

21. The system of claim 20, wherein the missing charge determiner determines the charge based on an afterglow decay constant of the detector array.

22. A method for approximating a signal indicative of detected radiation over a sampling interval, comprising:
generating pulses with a frequency indicative of an integration of the signal;
calculating a first contribution from a first pulse in the sampling interval to a last pulse in the sampling interval;
calculating a second contribution after the last pulse of the sampling interval to an end of the sampling interval based on a decay constant determined from the sampling interval; and
calculating, with processing electronics of an imaging system, a total contribution by adding the first and second contributions.

23. The method of claim 22, further including:
identifying whether the last pulse in the sampling interval aligns with an end of the sampling interval; and
calculating the second and total contributions when the last pulse does not align with the end of the sampling interval.

24. The method of claim 23, wherein a value of the total contribution is substantially equal to a value of the first contribution when the last pulse of the sampling interval aligns with the end of the sampling interval.

25. The method of claim 22, further including validating that the total contribution is substantially equal to a value of the integration.

* * * * *